United States Patent [19]

Porath

[11] Patent Number: 4,773,430
[45] Date of Patent: Sep. 27, 1988

[54] METHOD AND APPARATUS FOR THE LOCALIZATION OF BLEEDING IN THE GASTROINTESTINAL TRACT

[75] Inventor: Asher Porath, Jerusalem, Israel

[73] Assignee: Yissim Research Development Company, Jerusalem, Israel

[21] Appl. No.: 816,272

[22] Filed: Jan. 6, 1986

[30] Foreign Application Priority Data

Jan. 6, 1985 [IL] Israel ......................................... 74007

[51] Int. Cl.⁴ .............................................. A61M 1/00
[52] U.S. Cl. ..................................... 128/768; 128/638; 604/28; 604/35; 604/43
[58] Field of Search ................ 128/636, 637, 638, 768; 604/27, 28, 43, 35

[56] References Cited

U.S. PATENT DOCUMENTS

| | | | |
|---|---|---|---|
| 3,302,635 | 2/1967 | Pittman | 128/638 |
| 3,421,499 | 1/1969 | Bray et al. | 128/638 |
| 3,885,561 | 5/1975 | Cami | 604/280 |
| 4,294,251 | 10/1981 | Greenwald | 604/43 |
| 4,468,216 | 8/1984 | Muto | 604/43 |
| 4,525,156 | 6/1985 | Benusa et al. | 604/28 |
| 4,562,842 | 1/1986 | Morfeld et al. | 128/638 |

FOREIGN PATENT DOCUMENTS 2559205 7/1977 Fed. Rep. of Germany ........ 604/35

*Primary Examiner*—C. Fred Rosenbaum
*Assistant Examiner*—John D. Ferros
*Attorney, Agent, or Firm*—Cooper, Iver P.

[57] ABSTRACT

The present invention relates to a method for the localization of bleeding in the gastrointestinal tract. More particularly, the present invention relates to a method wherein gastric or intestinal contents at different locations in the gastrointestinal tract are continuously checked for their hemoglobin contents. The invention also relates to an apparatus adapted to carry out the method of the invention.

10 Claims, 1 Drawing Sheet

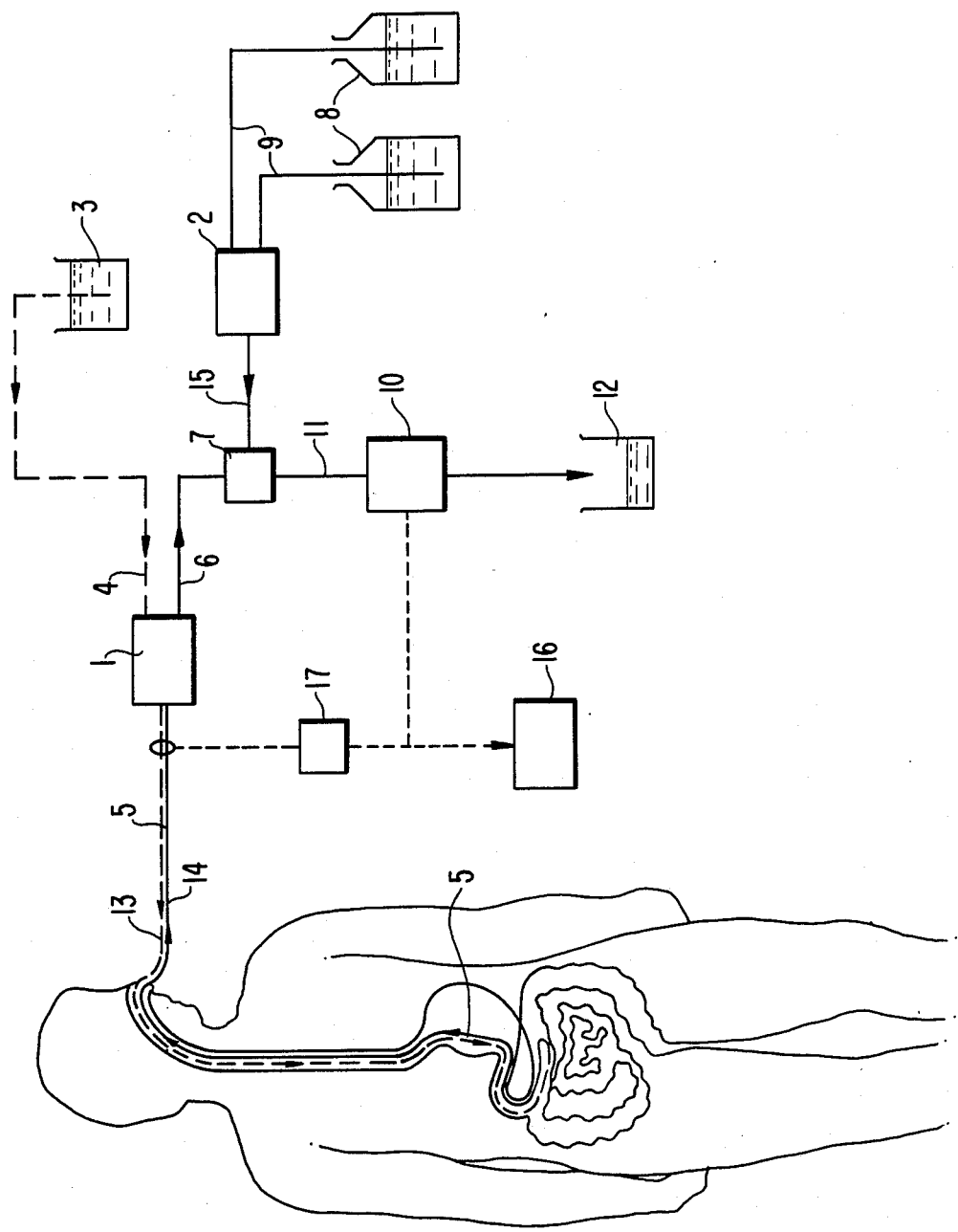

METHOD AND APPARATUS FOR THE LOCALIZATION OF BLEEDING IN THE GASTROINTESTINAL TRACT

Priority is claimed under 35 USC 119 from Israeli appl. No. 74,007, of Jan. 6, 1985.

FIELD OF THE INVENTION

The present invention relates to a method for the localization of bleeding in the gastrointestinal tract. More particularly, the present invention relates to a method wherein gastric or intestinal contents at different locations in the gastrointestinal tract are continuously checked for their hemoglobin contents. The invention also relates to an apparatus adapted to carry out the method of the invention.

BACKGROUND OF THE INVENTION

Tumour development at its early stages is usually accompanied by membrane breakdown and bleeding. Therefore, one of the first warnings of cancer in the gastrointestinal tract is blood lost into the stool. Methods have been developed to identify even microscopic amount of blood in feces by occult blood tests as outlined for example by Kutter et al. in Dtsch. Med. Wschr. 99(1974)2332. Such fecal occult blood tests enable to receive indication of tumoural development in its earliest stages, much before the patient has any complaints. This occult blood test in feces is an important tool for screening cancer in the gastrointestinal tract, i.e., the test identifies an attribute that may be linked to cancer in the gastrointestinal tract. However, such test does not give any indication as to the location of the bleeding. Furthermore, the presence of fecal blood may also result from non-cancerous conditions. Therefore, when bleeding is detected in feces, further diagnostic test must be carried out on the patient in order to identify the location and nature of the bleeding.

The diagnostic aids for the identification of the source of bleeding in the gastrointestinal tract which are most commonly used clinically are: gastroscopy, sigmoidoscopy, colonoscopy, duedenoscopy, selective abdominal angiography, double contrast barium anema, X-ray with contrasting material such as barium sulfide and ultrasonic imaging. The detection by all the above mentioned diagnostic aids is based on visualizing the bleeding lesion. Consequently, when the location of such lesion is detected an appropriate treatment can be chosen. Since surgical resection is the major mode of treatment for gastrointestinal tumours, it is of outmost importance to diagnose and localize gastrointestinal tumours at their earliest stage of development.

Unfortunately, in about 20 percent of the patients in which the occult blood test is positive, the location of bleeding by any of the above mentioned known diagnostic aids cannot be established. Some of the non diagnosed cases are accounted for by non-tumoural bleeding which will disappear after a lapse of time. However, other cases are due to tumoural bleeding in its earliest stages, while the small erosion of the membrane and the small amount of bleeding can not be viewed by any of the known diagnostic methods. Moreover, it is also known that in some cases of severe bleeding of the gastrointestinal tract, none of the known diagnostic aids detect the location of the bleeding due to obscureness. As a result, patients are sometimes taken to the operating table before a complete diagnosis has taken place for exploration inside and surgical resection is effected on organs suspected as being the source of bleeding, before complete confirmation of the localization of bleeding has been effected.

SUMMARY OF THE INVENTION

There has therefore been a long felt want for an independent method for the identification of the location of bleeding in the gastrointestinal tract, regardless of the location of the bleeding or its amount.

Accordingly, it is the object of the present invention to provide an effective method for the localization of bleeding in the gastrointestinal tract.

It is also the object of the present invention to provide an apparatus adapted for diagnosing the localization of bleeding in the gastrointestinal tract.

The method of the invention is based on the continuous measurement of the presence of hemoglobin along the gastrointestinal tract and comprises:

(a) introduction of a double-lumen tube into the gastrointestinal tract of a patient, (b) introduction of a physiological solution into the gastrointestinal tract through one of the tubes of said double-lumen tube, and simultaneous withdrawal of the physiological solution contaminated with gastric or intestinal fluid through the other tube of said double-lumen tube out of the body of the patient, (c) continuously testing said contaminated solution for the presence of hemoglobin, (d) changing the location of the end of said double-lumen tube in the gastrointestinal tract by measurable distances and repeating steps (b) and (c) above, (e) repeating step (d) above until hemoglobin test results reaches its maximum value and (f) measuring the depth of the double-lumen tube in the gastrointestinal tract.

DETAILED DESCRIPTION OF THE INVENTION

The invention also provides an apparatus for effecting said method, comprising:

(a) means for introducing and withdrawing a physiological solution into and from the gastrointestinal tract of a patient, and (b) means for continuously testing the withdrawn solution for the presence of hemoglobin.

The method and apparatus according to the invention allows detection of microscopic quantities of hemoglobin as low as 25 ppm.

The invention is illustrated, by way of example with reference to the accompanying drawing which is a schematic representation of the apparatus and the method embodying the present invention.

The FIGURE shows a two-way pump 1 connected via conduit 4 to a saline solution container 3 and to a double lumen tube 5. Pump 1 is also connected to mixing head 7 via conduit 6. Double lumen tube 5 is composed of tubes 13 and 14 and it is adapted to be inserted into the gastrointestinal tract of the human body. Another two-way pump 2 is connected to reagent bottles 8 via conduits 9 and to mixing head 7 via conduit 15. Mixing head 7 is connected to detector 10 via conduit 11. A drainage container 12 is provided for collecting drainage from the detector 10.

In accordance with the invention, the double lumen tube 5 is introduced into the gastrointestinal tract of a patient until the desired depth in tract is reached. Tube 5 can be introduced into the gastrointestinal tract through any one of the natural body openings which communicate with it, i.e., mouth, nose or anus. Introduction into the colon through the anus is effected with the aid of a suitable device such as a colonoscope. Then saline solution is flowed from container 3 by pump 1 through tube 13 of double lumen tube 5 into the gastrointestinal tract. Simultaneously, the saline contaminated with gastric or intestine contents is pumped out of the gastrointestinal tract through tube 14 of double-lumen tube 5 and transferred to the mixing head 7 by conduit 6. Reagents capable of reacting with hemoglobin and forming an easily detectable compound are pumped out of reagent bottles 8 by pump 2 and enter the mixing head 7 through conduit 15. The mixture in the mixing head 7 is then driven by pumps 1 and 2 via conduit 11 to detector 10 from which it flows to drainage container 12.

Detector 10 may be connected to recorder 16 for continuous recording of the presence or the absence of the hemoglobin. A length sensor 17, connected between double lumen tube 5 and recorder 16, may be provided enabling the recording of the presence of hemoglobin versus tube length.

An alarm system (not shown) may also be connected to detector 10 for an audible indication of the presence or absence of hemoglobin.

Detector 10 can be any conventional detector capable of detecting the compound formed in the mixing head in the presence of hemoglobin. Preferably, the detector according to the invention, is a colourimeter or a photometer, such as Spectronics 20 (Baush & Lomb Co.).

Any reagent capable of reacting with hemoglobin and forming an easily detectable compound is suitable for use in method and apparatus according to the invention. Preferred reagents are o-tolidine, as employed in the procedure described by R. M. Jaffe & W. Zierdt in J. Lab. Clin. Med. 93, 879–886, 1979, or 4-amino phenazone, as employed in the procedure described by K. Bauer in J. Clin. Chem. Clin. Biochem. 19, 971–976, 1981. When the amino phenazone reagent is used, a solution of the reagent is contained in one of the bottles 8 and a buffer solution containing Hydrogen Peroxide is contained in the other bottle 8. When hemoglobin is present in the mixing head and reagents are pumped into the mixing head, a coloured compound is formed. Conduit 11 should be long enough to provide the chemical reaction sufficient time to develop the coloured component.

Pumps 1 and 2 can be any two-way pump. A multichannel pump can also be employed. Preferably a peristaltic pump such as Model PLG by Desaga are employed.

Double lumen tube 5 can be any conventional long double lumen or feeding tube used in gastrointestinal treatment or diagnosis. However, the double lumen tube has to have the two openings at the measuring end in close proximity to each other. Preferably, the tube is made of an X-ray opaque material and is graduated to allow for the exact location of the tube in the gastrointestinal tract. For example an Andersen tube AN20 by H. W. Andersen Products Ltd. is a suitable double lumen tube.

As stated above, the double-lumen tube can be introduced into the gastrointestinal tract from any of its natural openings, i.e., through the nose, mouth or anus. Preferably a nasal entry tube is used. Before insertion, the posterior pharynx and the base of the tongue are treated with an appropriate topical anesthetic and nasal cavity is lubricated with an aqueous lubricating jelly. The tube is then passed through the nasal cavity and swallowed by the patient. The tube advances as the larynx rises during swallowing. At the depth of 75 cm. with the aid of a syringe, aspirant is withdrawn and checked with litmus paper; if it is alkaline the tube can be advanced further. The patient should swallow continuously and breath deeply while the tube is slowly advanced into the esophagus and stomach. The tube is further moved along the intestine by peristalsis.

Preferably, progress of the tube in the gastrointestinal tract is monitored by X-ray. X-ray monitoring of the progress of tube should be at frequent intervals.

When the tube has reached the desired depth the measurement can start. The two lumens of the tube are then connected separately with the apparatus of the invention. Through one of the lumens the apparatus pumps in sterile saline solution at the rate of 1 ml/min and simultaneously, from the second lumen, saline which became contaminated with the intestinal fluid is withdrawn. The withdrawn liquid is mixed in the mixing head with 4-aminophenazone 0.57 gr/l+Phenol 9 gr/l 1:1 and with 1.5% Hydrogen Peroxide in buffer Phosphate in equal amounts. From the mixing head, the mixture passes through a suitable long tubing to allow the chemical reaction sufficient time to develop the coloured component if hemoglobin is present in the mixture. From this tubing, the mixture enters a colourimeter which measures the colour intensity developed in the mixture. For variation from 25 to 100 ppm blood, the Optical Density varies 0.6 units. The colour intensity may be displayed by Spectronic 20 (Baush & Lomb Co.) colourimeter and recorded by a strip chart recorder. When there is a positive colour reading an alarm signal is generated. The end of the double lumen tube, when the reading is highest, is at the site of bleeding. This location can be reached twice within one test: once, while the tube penetrates into the intestinal tract and a second time when the tube is withdrawn in a stepwise manner. The location is then identified by the length of the tube measured from the nose of the patient, and by X-ray.

The advantages of the present invention will become apparent from the following clinical example:

A 68 years old male underwent partial gastrectomy because of a peptic ulcer. During the two years following the operation, the patient complained of black stool (melena). Although melena indicated that the source of the bleeding was in the upper part of the gastrointestinal tract, attempts to localize the bleeding during repeated hospitalizations were fruitless. The patient had to receive one unit of blood every two weeks during this two-year-period. He was readmitted to the hospital and underwent the routine clinical tests, X-raying of the whole length of the gastrointestinal tract with contrast material (gastrographine, barium) gastroscopy, colonoscopy, angiography and investigation by nuclear medicine. None of the above common diagnostic tests allowed localization of the source of bleeding. The patient was then investigated 3 times in a two-day-period by the method according to the invention. On two occasions, the afferent side of the intestinal tract was entered with the double lumen tube and decreasing amounts of blood from the anastomosis downward were found. No blood was found in the stomach. On the third attempt the afferent side was entered from the anastomosis. In this test bleeding was found at 120 cm depth as measured from the nose of the patient and an X-ray picture was taken. The tube was introduced into the afferent portion under X-rays while turning the lying patient to his right side and to his back, back and forth. After this finding, gastroscopy, which was proved negative two days before, was repeated and focused to the location indicated by the method according to the invention and a lesion was found near the Vater's papilla. The patient was operated and a tumor was found on the head of the pancreas which infiltrated into the gut.

I claim:

1. A method for the localization of bleeding in the gastrointestinal tract comprising:
   (a) introduction of a double lumen tube into the gastrointestinal tract of a patient,
   (b) introduction of a physiological solution into the gastrointestinal tract through one of the tubes of said double-lumen tube, and simultaneous withdrawal of the physiological solution contaminated with gastric or intestinal fluid through the other tube of said double-lumen tube out of the body of the patient,
   (c) continuously testing said contaminated solution for the presence of hemoglobin,
   (d) changing the location of the end of said double-lumen tube in the gastrointestinal tract by a measurable distance and repeating steps (b) and (c) above,
   (e) ascertaining the depth of tube penetration into the gastrointestinal tract at which the level of hemoglobin in the contaminated solution was maximal.

2. The method according to claim 1, wherein the double-lumen tube is introduced into the gastrointestinal tract through the nose or mouth.

3. The method according to claim 1, wherein the double-lumen tube is introduced into the gastrointestinal tract through the rectum and hemoglobin tests are carried out while said tube is introduced or slowly pulled out.

4. The method according to claim 1, in which the exact position of the tube within the patient's gastrointestinal tract is determined by X-ray examination.

5. An apparatus for determining the location of bleeding in the gastrointestinal tract comprising:
   (a) means for introducing and withdrawing a physiological solution into and from the gastrointestinal tract of a patient at equal flow rates, and
   (b) means for continuously testing the withdrawn solution for the presence of hemoglobin;
the means of paragraphs (a) and (b) further comprising:
   (i) a mixing head;
   (ii) a first pump means adapted to introduce saline into the gastrointestinal tract of patient through a double lumen tube and to withdraw contaminated saline from the gastrointestinal tract into said mixing head;
   (iii) a second pump means adapted to introduce reagents which react with hemoglobin to form a detectable product into said mixing head; and
   (iv) a detector for detecting the chemical reaction product.

6. An apparatus according to claim 5 further comprising a recorder connected to the detector for continuous recording of the hemoglobin contents along the gastrointestinal tract.

7. An apparatus according to claim 5 further comprising an alarm system connected to the detector.

8. An apparatus according to claim 5, wherein the means for introducing and withdrawing a solution is radioopaque.

9. The apparatus of claim 7 in which the detector is a colorimeter.

10. A method for the localization of bleeding in the gastrointestinal tract, which comprises continuously sampling gastric or intestinal fluids from the tract without diminishing GI fluid volume while continuously moving a sampling means along the tract, testing the samples for hemoglobin content, and ascertaining the point in the tract where the sample having the highest hemoglobin content was taken.

* * * * *

UNITED STATES PATENT AND TRADEMARK OFFICE
CERTIFICATE OF CORRECTION

PATENT NO. : 4,773,430

DATED : September 27, 1988

INVENTOR(S) : Porath, et al

It is certified that error appears in the above-identified patent and that said Letters Patent is hereby corrected as shown below:

Col. 2, lines 38 and 39, delete the subtitle, and insert that subtitle --DETAILED DESCRIPTION OF THE INVENTION--before the paragraph beginning in Column 2 at the line numbered 50.

Signed and Sealed this

Fourteenth Day of August, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,773,430
DATED : September 27, 1988
INVENTOR(S) : Porath, et al

It is certified that error appears in the above-identified patent and that said Letters Patent is hereby corrected as shown below:

On the title page assignee should read

--(73) Assignee: Yissin Research Development Company of the Hebrew Univversity of Jerusalem, Jerusalem, Israel--.

Signed and Sealed this

Eleventh Day of September, 1990

Attest:

HARRY F. MANBECK, JR.

*Attesting Officer*  *Commissioner of Patents and Trademarks*